US00PP26246P2

(12) United States Plant Patent
Verhoef

(10) Patent No.: US PP26,246 P2
(45) Date of Patent: Dec. 22, 2015

(54) ***PHYSOCARPUS* PLANT NAMED 'BERT DART'S G'**

(50) Latin Name: *Physocarpus opulifolius*
Varietal Denomination: Bert Dart3 G

(71) Applicant: Gijsbertus Verhoef, Hazerswoude (NL)

(72) Inventor: Gijsbertus Verhoef, Hazerswoude (NL)

( * ) Notice: Subject to any disclaimer, the term of this patent is extended or adjusted under 35 U.S.C. 154(b) by 151 days.

(21) Appl. No.: 13/998,223

(22) Filed: Oct. 11, 2013

(51) Int. Cl.
*A01H 5/02* (2006.01)

(52) U.S. Cl.
USPC ..... Plt./226

(58) Field of Classification Search
USPC ..... Plt./226
See application file for complete search history.

(56) References Cited

U.S. PATENT DOCUMENTS

| | | | | |
|---|---|---|---|---|
| PP16,371 | P2 * | 3/2006 | Davasse | Plt./226 |
| PP16,894 | P2 * | 7/2006 | Pellett | Plt./226 |
| PP21,560 | P2 * | 12/2010 | Schuurbiers | Plt./226 |
| PP23,177 | P2 * | 11/2012 | Durand | Plt./226 |

* cited by examiner

*Primary Examiner* — Anne Grunberg
(74) *Attorney, Agent, or Firm* — C. A. Whealy

(57) ABSTRACT

A new and distinct cultivar of *Physocarpus* plant named 'Bert Dart's G', characterized by its compact and mounded plant habit; freely branching habit; dense and bushy habit; yellow to yellow green-colored leaves; showy inflorescences with numerous white-colored flowers; good garden performance; and resistance to Powdery Mildew.

2 Drawing Sheets

Botanical designation: *Physocarpus opulifolius.*
Cultivar denomination: 'BERT DART'S G'.

BACKGROUND OF THE INVENTION

The present invention relates to a new and distinct *Physocarpus* plant, botanically known as *Physocarpus opulifolius* and hereinafter referred to by the name 'Bert Dart's G'.

The new *Physocarpus* plant is a product of a controlled breeding program conducted by the Inventor in Hazerswoude, The Netherlands. The objective of the breeding program is to create new compact *Physocarpus* plants with yellow green-colored leaves and resistance to Powdery Mildew.

The new *Physocarpus* plant originated from an open-pollination in June, 2008 in Hazerswoude, The Netherlands of *Physocarpus opulifolius* 'Dart's Gold', not patented, as the female, or seed, parent with an unknown selection of *Physocarpus opulifolius* as the male, or pollen, parent. The new *Physocarpus* plant was discovered and selected by the Inventor in May, 2010 as a single flowering plant within the progeny of the stated open-pollination in a controlled environment in Hazerswoude, The Netherlands.

Asexual reproduction of the new *Physocarpus* plant by softwood cuttings in a controlled environment in Hazerswoude, The Netherlands since May, 2010 has shown that the unique features of this new *Physocarpus* plant are stable and reproduced true to type in successive generations of asexual reproduction.

SUMMARY OF THE INVENTION

Plants of the new *Physocarpus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Bert Dart's G'. These characteristics in combination distinguish 'Bert Dart's G' as a new and distinct *Physocarpus* plant:

1. Compact and mounded plant habit.
2. Freely branching habit; dense and bushy habit.
3. Yellow to yellow green-colored leaves.
4. Showy inflorescences with numerous white-colored flowers.
5. Good garden performance.
6. Resistant to Powdery Mildew.

Plants of the new *Physocarpus* can be compared to plants of the female parent, 'Dart's Gold'. Plants of the new *Physocarpus* differ from plants of 'Dart's Gold' in the following characteristics:

1. Plants of the new *Physocarpus* are more compact than plants of 'Dart's Gold'.
2. Plants of the new *Physocarpus* are more resistant to Powdery Mildew than plants of 'Dart's Gold'.

Plants of the new *Physocarpus* can be compared to plants of the *Physocarpus* 'Nugget', not patented. In side-by-side comparisons conducted in Hazerswoude, The Netherlands, plants of the new *Physocarpus* differed from plants of 'Nugget' in the following characteristics:

1. Plants of the new *Physocarpus* were more compact than plants of 'Nugget'.
2. Plants of the new *Physocarpus* were more mounded than and not as arching as plants of 'Nugget'.
3. Plants of the new *Physocarpus* and 'Nugget' differed in leaf color.
4. Plants of the new *Physocarpus* were more resistant to Powdery Mildew than plants of 'Nugget'.

BRIEF DESCRIPTION OF THE PHOTOGRAPHS

The accompanying colored photographs illustrate the overall appearance of the new *Physocarpus*, showing the colors as true as it is reasonably possible to obtain in colored reproductions of this type. Colors in the photographs may differ slightly from the color values cited in the detailed botanical description which accurately describe the colors of the new *Physocarpus*.

The photograph on the first sheet is a side perspective view of a typical flowering plant of 'Bert Dart's G' grown in an outdoor nursery.

The photograph on the second sheet is a close-up view of a typical flowering plant of 'Bert Dart's G'.

DETAILED BOTANICAL DESCRIPTION

The aforementioned photographs and following observations, measurements and values describe plants grown during the summer in ground beds in an outdoor nursery in Grand Haven, Mich. and under cultural practices typical of commercial production. Plants were three years old when the photographs and the description were taken. In the description, color references are made to The Royal Horticultural Society Colour Chart, 1995 Edition, except where general terms of ordinary dictionary significance are used.

Botanical classification: *Physocarpus opulifolius* 'Bert Dart's G'.

Parentage:

*Female, or seed, parent.*—*Physocarpus opulifolius* 'Dart's Gold', not patented.

*Male, or pollen, parent.*—Unknown selection of *Physocarpus opulifolius*, not patented.

Propagation:

*Type.*—By softwood cuttings.

*Time to initiate roots, summer.*—About 20 days at 20° C.

*Time to produce a rooted young plant, summer.*—About three months at 20° C.

*Root description.*—Fine to thick; fibrous; white and brown in color.

*Rooting habit.*—Freely branching; dense.

Plant description:

*Plant and growth habit.*—Perennial shrub; compact and mounding plant habit; vigorous growth habit.

*Branching habit.*—Freely branching habit with about 65 lateral branches developing per plant; pinching enhances lateral branch development.

*Plant height.*—About 63 cm.

*Plant diameter* (*area of spread*).—About 100 cm.

Lateral branch description:

*Length.*—About 15 cm.

*Diameter.*—About 3 mm.

*Internode length.*—About 1 cm.

*Texture.*—Smooth, glabrous.

*Color, developing.*—Close to 144D becoming closer to 176C with development.

*Color, developed.*—Close to 197D.

Leaf description:

*Arrangement.*—Alternate, simple.

*Length.*—About 6.5 cm.

*Width.*—About 4.5 cm.

*Shape.*—Ovate; tri-lobed.

*Apex.*—Acute.

*Base.*—Obtuse.

*Margin.*—Lobed; crenate to dentate.

*Texture, upper and lower surfaces.*—Smooth, glabrous.

*Venation pattern.*—Pinnate.

*Color.*—Developing leaves, upper surface: High light levels, close to 150B; low light levels, closer to 144A. Developing leaves, lower surface: High light levels, close to 150C; low light levels, closer to 147B. Fully expanded leaves, upper surface: High light levels, close to 1C to 150B; low light levels, closer to 147A; venation, close to 144B. Fully expanded leaves, lower surface: High light levels, close to 150C; low light levels, closer to 147B; venation, close to 144B.

*Petioles.*—Length: About 1.5 cm. Diameter: About 2 mm. Texture, upper and lower surfaces: Smooth, glabrous. Color, upper and lower surfaces: Close to 144D.

Flower description:

*Flower appearance and arrangement.*—Single rotate flowers arranged in terminal and axillary corymbs; corymbs hemispherical in shape; freely flowering habit with usually about 34 flowers per inflorescence and about 442 flowers developing per lateral branch; flowers face upright to outwardly.

*Flower longevity.*—Flowers last for about three to four weeks on the plant; flowers not persistent.

*Natural flowering season.*—Plants flower from late May though June in Michigan.

*Fragrance.*—None detected.

*Inflorescence height.*—About 3 cm.

*Inflorescence diameter.*—About 3 cm.

*Flower diameter.*—About 8 mm.

*Flower length* (*height*).—About 6 mm.

*Flower buds.*—Length: About 2 mm. Diameter: About 2 mm. Shape: Elliptical to obovate. Color: Close to between 145A and 155C.

*Petals.*—Quantity and arrangement: Five petals in a single whorl. Length: About 4 mm. Width: About 3.5 mm. Shape: Elliptic to obovate. Apex: Obtuse. Margin: Entire. Texture, upper and lower surfaces: Smooth, glabrous. Color, when opening, upper and lower surfaces: Close to 155D. Color, fully opened, upper and lower surfaces: Close to 155D.

*Sepals.*—Quantity and arrangement: Five in a single whorl. Length: About 1 mm. Width: About 2 mm. Shape: Subulate. Apex: Acute. Margin: Entire. Texture, upper and lower surfaces: Smooth, glabrous. Color, when opening, upper and lower surfaces: Close to 144D. Color, fully opened, upper and lower surfaces: Close to 144D.

*Peduncles.*—Length: About 3 cm. Diameter: About 1 mm. Strength: Strong. Texture: Smooth, glabrous. Color: Close to 144D.

*Pedicels.*—Length: About 2 mm. Diameter: About 1 mm. Strength: Strong. Texture: Smooth, glabrous. Color: Close to 144D.

*Reproductive organs.*—Androecium: Quantity per flower: About 20. Anther length: About 0.5 mm. Anther shape: Oblong. Anther color: Close to 176A. Amount of pollen: Scarce. Pollen color: Close to 156A. Gynoecium: Quantity per flower: About four. Pistil length: About 1 mm. Style length: About 0.6 mm. Style color: Close to 145B. Stigma appearance: Globular. Stigma color: Close to 145B. Ovary color: Close to 145B.

*Seeds and fruits.*—Seed and fruit development have not been observed on plants of the new *Physocarpus* plant.

Garden performance: Plants of the new *Physocarpus* have been observed to have good garden performance and to tolerate rain, wind and temperatures ranging from about −25° C. to about 35° C.

Pathogen & pest resistance: Plants of the new *Physocarpus* have been observed to be resistant to Powdery Mildew. Plants of the new *Physocarpus* have not been shown to be resistant to pests and other pathogens common to *Physocarpus* plants.

It is claimed:

1. A new and distinct *Physocarpus* plant named 'Bert Dart's G' as illustrated and described.

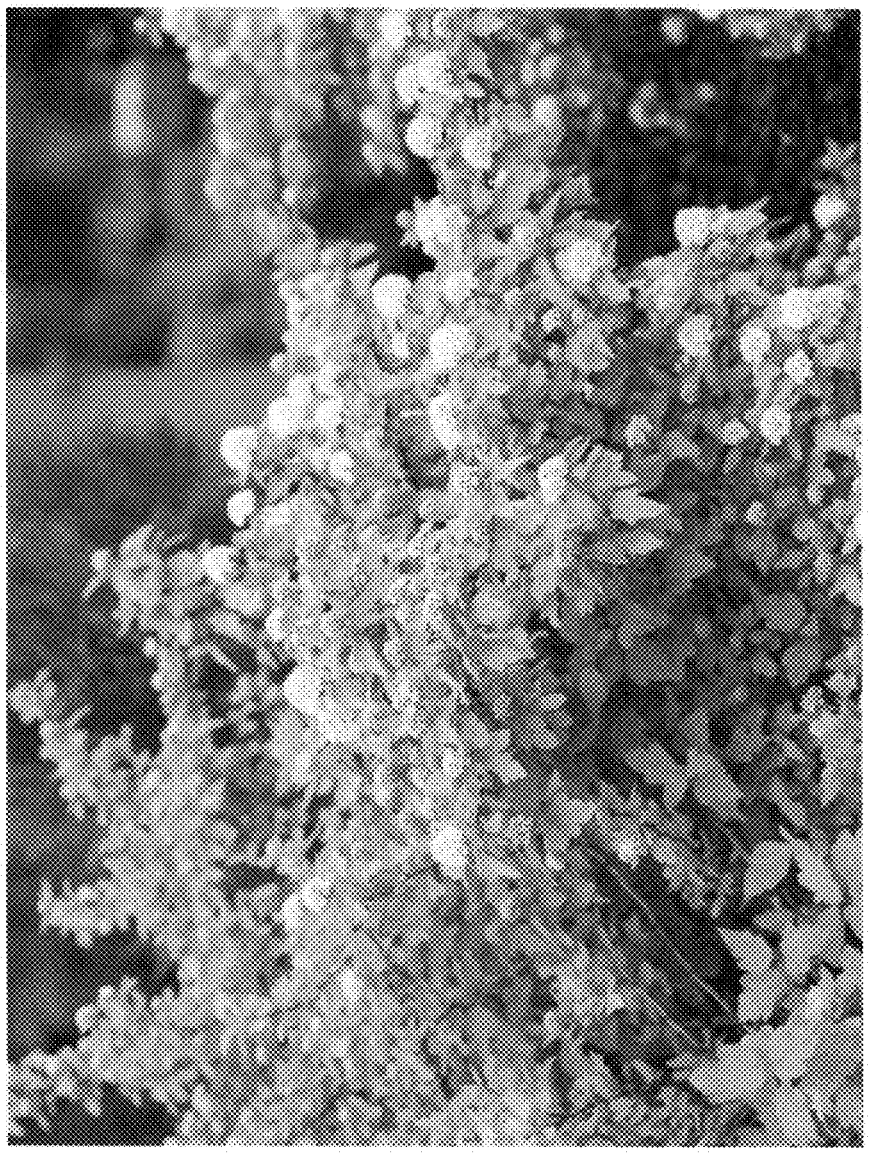

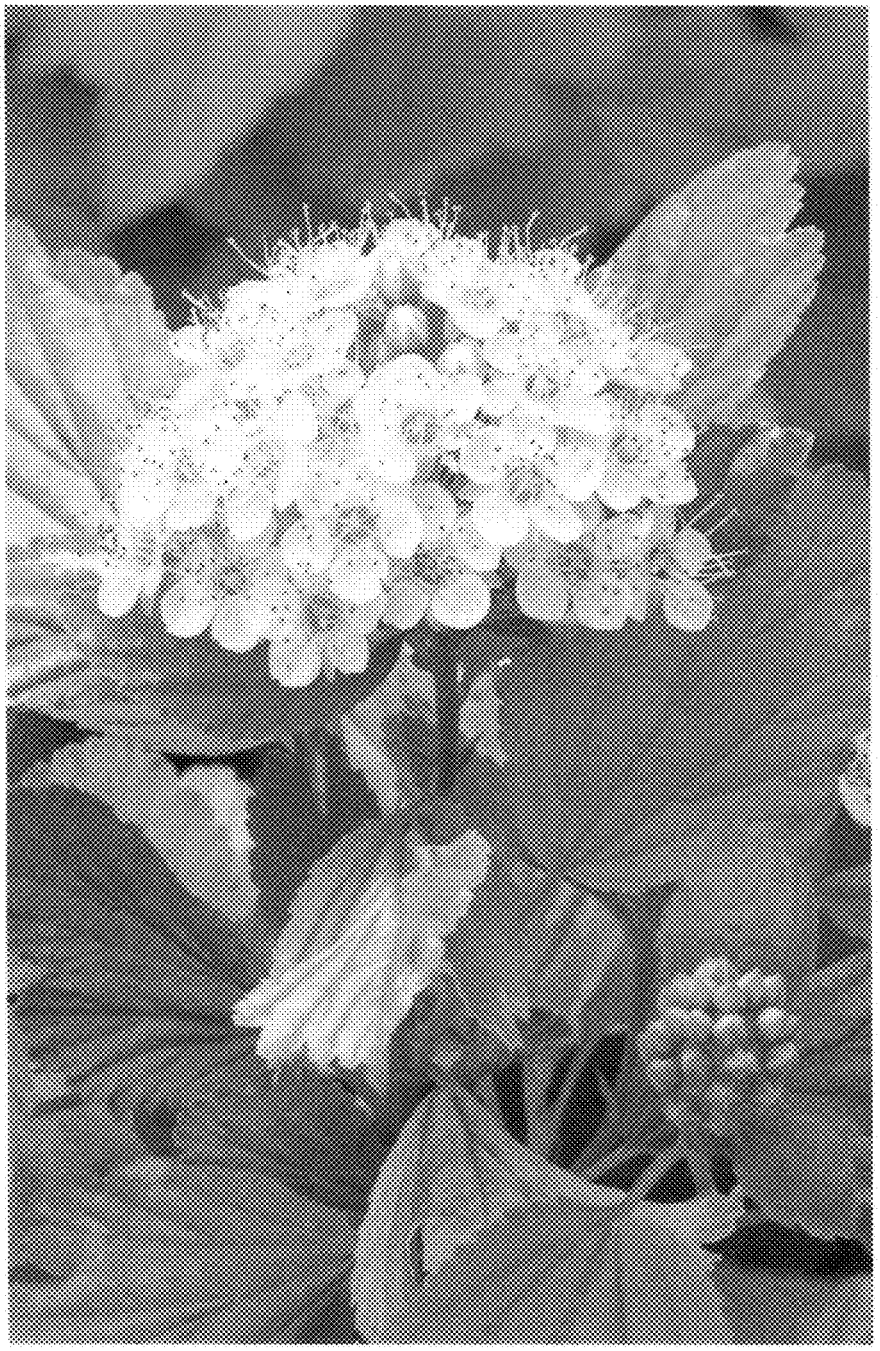

* * * * *